(12) United States Patent
Devengenzo et al.

(10) Patent No.: US 10,500,006 B2
(45) Date of Patent: Dec. 10, 2019

(54) CONSTANT FORCE SPRING WITH ACTIVE BIAS

(71) Applicant: Intuitive Surgical Operations, Inc., Sunnyvale, CA (US)

(72) Inventors: Roman L. Devengenzo, San Jose, CA (US); Paul G. Griffiths, Santa Clara, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 16/193,653

(22) Filed: Nov. 16, 2018

(65) Prior Publication Data

US 2019/0083184 A1 Mar. 21, 2019

Related U.S. Application Data

(63) Continuation of application No. 15/121,341, filed as application No. PCT/US2015/020878 on Mar. 17, 2015, now Pat. No. 10,201,393.

(Continued)

(51) Int. Cl.
*F16M 11/00* (2006.01)
*A61B 34/35* (2016.01)
(Continued)

(52) U.S. Cl.
CPC .............. *A61B 34/35* (2016.02); *A61B 34/30* (2016.02); *A61B 90/50* (2016.02); *B25J 9/0033* (2013.01);
(Continued)

(58) Field of Classification Search
CPC ........... F16M 2200/027; F16M 11/046; F16M 2200/028; F16M 11/2021
(Continued)

(56) References Cited

U.S. PATENT DOCUMENTS

| | | | |
|---|---|---|---|
| 3,893,263 A | * | 7/1975 | Jackman ................. B24B 23/08 451/246 |
| 4,604,787 A | | 8/1986 | Sievers, Jr. |

(Continued)

FOREIGN PATENT DOCUMENTS

| | | |
|---|---|---|
| CN | 202599962 U | 12/2012 |
| JP | S60262201 A | 12/1985 |
| WO | WO-2014028699 A1 | 2/2014 |

OTHER PUBLICATIONS

International Search Report and Written Opinion for Application No. PCT/US15/20878, dated Jul. 14, 2015, 13 pages.

(Continued)

*Primary Examiner* — Steven M Marsh

(57) ABSTRACT

A compensated constant force spring device includes a bracket, a drum rotatably supported by the bracket, and a constant force spring wound on the drum. A motor is fixed to the bracket and provides a compensating force to the drum. The motor may be located in an interior volume of the drum. A control module may coupled to the motor to control the compensating force. A position sensor may be coupled to the control module. The compensating force may be responsive to a signal from the position sensor. The constant force spring may support a load and counterbalance gravitational forces on the load. The compensating force may be adjusted when the load approaches an end of a range of travel.

21 Claims, 7 Drawing Sheets

Related U.S. Application Data

(60) Provisional application No. 61/954,452, filed on Mar. 17, 2014, provisional application No. 62/019,311, filed on Jun. 30, 2014.

(51) Int. Cl.
*A61B 90/50* (2016.01)
*A61B 34/30* (2016.01)
*F16M 13/02* (2006.01)
*B25J 9/00* (2006.01)
*B25J 9/16* (2006.01)
*B25J 19/00* (2006.01)
*A61B 90/00* (2016.01)

(52) U.S. Cl.
CPC ......... *B25J 9/1689* (2013.01); *B25J 19/0004* (2013.01); *F16M 13/022* (2013.01); *A61B 90/03* (2016.02); *A61B 2090/5025* (2016.02)

(58) Field of Classification Search
USPC ....... 248/584, 586, 590, 592, 594, 599, 600, 248/601, 610, 644, 579, 580, 334.1, 335, 248/336, 337, 338, 331, 332, 333, 330.1
See application file for complete search history.

(56) References Cited

U.S. PATENT DOCUMENTS

| | | | |
|---|---|---|---|
| 4,943,020 A | 7/1990 | Beaucoup et al. | |
| 5,279,309 A | 1/1994 | Taylor et al. | |
| 5,784,542 A | 7/1998 | Ohm et al. | |
| 5,923,139 A | 7/1999 | Colgate et al. | |
| 6,120,433 A | 9/2000 | Mizuno et al. | |
| 6,367,757 B1* | 4/2002 | Aramaki | E04B 9/006 248/327 |
| 6,393,340 B2 | 5/2002 | Funda et al. | |
| 6,434,507 B1 | 8/2002 | Clayton et al. | |
| 6,484,993 B2* | 11/2002 | Huffman | F16M 11/046 248/323 |
| 6,493,608 B1 | 12/2002 | Niemeyer | |
| 6,645,196 B1 | 11/2003 | Nixon et al. | |
| 7,883,458 B2 | 2/2011 | Hamel | |
| 8,191,322 B2* | 6/2012 | Liestenfeltz | H01Q 1/1235 212/296 |
| 8,357,144 B2 | 1/2013 | Whitman et al. | |
| 8,506,556 B2 | 8/2013 | Schena | |
| 8,749,190 B2 | 6/2014 | Nowlin et al. | |
| 9,267,639 B2* | 2/2016 | Sweere | F16M 11/30 |
| 9,358,074 B2 | 6/2016 | Schena et al. | |
| 1,002,879 A1 | 7/2018 | Griffiths et al. | |
| 2002/0032452 A1 | 3/2002 | Tierney et al. | |
| 2003/0139753 A1 | 7/2003 | Wang et al. | |
| 2005/0193451 A1 | 9/2005 | Quistgaard et al. | |
| 2006/0106493 A1 | 5/2006 | Niemeyer et al. | |
| 2007/0142701 A1 | 6/2007 | Goldberg et al. | |
| 2007/0142825 A1 | 6/2007 | Prisco et al. | |
| 2007/0299427 A1 | 12/2007 | Yeung et al. | |
| 2008/0046122 A1 | 2/2008 | Manzo et al. | |
| 2008/0200794 A1 | 8/2008 | Teichman et al. | |
| 2009/0062813 A1 | 3/2009 | Prisco et al. | |
| 2009/0076368 A1 | 3/2009 | Balas | |
| 2009/0076476 A1 | 3/2009 | Barbagli et al. | |
| 2009/0145241 A1 | 6/2009 | Cowgill | |
| 2009/0163929 A1 | 6/2009 | Yeung et al. | |
| 2010/0228264 A1 | 9/2010 | Robinson et al. | |
| 2010/0228588 A1 | 9/2010 | Nielsen et al. | |
| 2010/0274087 A1 | 10/2010 | Diolaiti et al. | |
| 2011/0082452 A1 | 4/2011 | Melsky et al. | |
| 2011/0277236 A1 | 11/2011 | Moriarity et al. | |
| 2011/0295248 A1 | 12/2011 | Wallace et al. | |
| 2011/0319714 A1 | 12/2011 | Roelle et al. | |
| 2011/0319815 A1 | 12/2011 | Roelle et al. | |
| 2012/0224673 A1 | 9/2012 | Barker et al. | |
| 2013/0096574 A1 | 4/2013 | Kang et al. | |
| 2013/0223598 A1 | 8/2013 | Simmons et al. | |
| 2014/0031983 A1 | 1/2014 | Low et al. | |
| 2014/0039517 A1 | 2/2014 | Bowling et al. | |
| 2014/0039681 A1 | 2/2014 | Bowling et al. | |
| 2014/0052153 A1 | 2/2014 | Griffiths et al. | |
| 2014/0052154 A1 | 2/2014 | Griffiths et al. | |
| 2014/0222207 A1 | 8/2014 | Bowling et al. | |
| 2016/0367334 A1 | 12/2016 | Devengenzo et al. | |
| 2018/0318023 A1 | 11/2018 | Griffiths et al. | |

OTHER PUBLICATIONS

International Search Report and Written Opinion for Application No. PCT/US15/21047, dated Jun. 8, 2015, 13 pages.

Extended European Search Report for Application No. 15764074.9, dated Oct. 11, 2017, 6 pages.

Extended European Search Report for Application No. 15765708.1, dated Oct. 16, 2017, 8 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

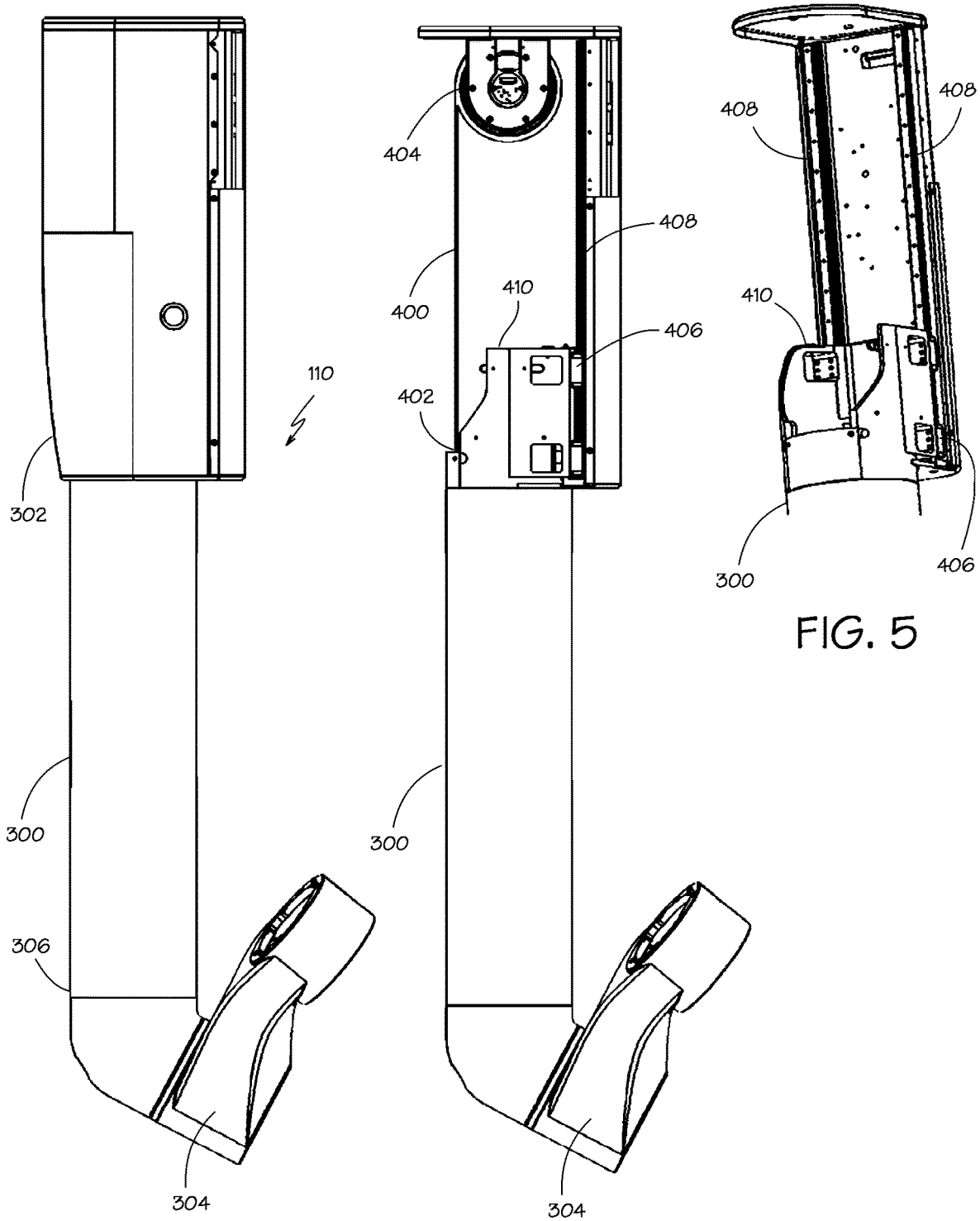

CONSTANT FORCE SPRING WITH ACTIVE BIAS

CROSS-REFERENCE TO RELATED APPLICATIONS

This application is a continuation of U.S. patent application Ser. No. 15/121,341 filed Aug. 24, 2016, which is a 371 of international application number PCT/US2015/020878 filed Mar. 17, 2015, and is related to and claims benefit of U.S. Provisional Application No. 61/954,452 filed Mar. 17, 2014, entitled "CONSTANT FORCE SPRING WITH ACTIVE BIAS"; and U.S. Provisional Application No. 62/019,311 filed Jun. 30, 2014, entitled "CONSTANT FORCE SPRING WITH ACTIVE BIAS", each of which are incorporated herein by reference in their entirety and for all purposes.

FIELD

Embodiments of the invention relate to the field of field of constant force springs; and more specifically, to constant force springs with an active bias for supporting surgical instruments at an adjustable height.

BACKGROUND

Minimally invasive medical techniques have been used to reduce the amount of extraneous tissue which may be damaged during diagnostic or surgical procedures, thereby reducing patient recovery time, discomfort, and deleterious side effects. Traditional forms of minimally invasive surgery include endoscopy. One of the more common forms of endoscopy is laparoscopy, which is minimally invasive inspection or surgery within the abdominal cavity. In traditional laparoscopic surgery, a patient's abdominal cavity is insufflated with gas and cannula sleeves are passed through small (approximately 1¼ cm.) incisions in the musculature of the patient's abdomen to provide entry ports through which laparoscopic surgical instruments can be passed in a sealed fashion.

The laparoscopic surgical instruments generally include a laparoscope for viewing the surgical field and working tools defining end effectors. Typical surgical end effectors include clamps, graspers, scissors, staplers, and needle holders, for example. The working tools are similar to those used in conventional (open) surgery, except that the working end or end effector of each tool is separated from its handle by an approximately 30 cm. long extension tube, for example, so as to permit the operator to introduce the end effector to the surgical site and to control movement of the end effector relative to the surgical site from outside a patient's body.

In order to provide improved control of the working tools, it may be desirable to control the instrument with teleoperated actuators. The surgeon may operate controls on a console to indirectly manipulate the instrument that is connected to the teleoperated actuators. The instrument is detachably coupled to the teleoperated actuators so that the instrument can be separately sterilized and selected for use as needed instrument for the surgical procedure to be performed. The instrument may be changed during the course of a surgery.

Performing surgery with teleoperated actuated instruments creates new challenges. One such challenge is providing a teleoperated motor mechanism that supports the teleoperated actuated surgical instruments that can be positioned with respect to the patient. These mechanisms are fairly heavy, weighing perhaps twelve to twenty-four kilograms. The mechanisms must be moved over a patient and positioned carefully. Therefore it is necessary to counterbalance the surgical instrument, the related actuators, and the support structure so that the surgical instrument can safely and easily be positioned. Counterbalancing is made more difficult because the various surgical instruments may have various weights.

It would be desirable to provide a way of counterbalancing a surgical instrument, its related actuators, and support structure that is effective with changeable surgical instruments of various weights.

SUMMARY

A compensated constant force spring device includes a bracket, a drum rotatably supported by the bracket, and a constant force spring wound on the drum. A motor is fixed to the bracket and provides a compensating force to the drum. The motor may be located in an interior volume of the drum. A control module may coupled to the motor to control the compensating force. A position sensor may be coupled to the control module. The compensating force may be responsive to a signal from the position sensor. The constant force spring may support a load and counterbalance gravitational forces on the load. The compensating force may be adjusted when the load approaches an end of a range of travel.

Other features and advantages of the present invention will be apparent from the accompanying drawings and from the detailed description that follows below.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements:

FIG. 3 is a side view of setup joint for a surgical instrument.

FIG. 4 is a side view of the setup joint shown in FIG. 3 with a housing removed.

FIG. 5 is a perspective view of a portion of the setup joint shown in FIG. 4.

DESCRIPTION OF EMBODIMENTS

In the following description, numerous specific details are set forth. However, it is understood that embodiments of the invention may be practiced without these specific details. In other instances, well-known circuits, structures, and techniques have not been shown in detail in order not to obscure the understanding of this description.

In the following description, reference is made to the accompanying drawings, which illustrate several embodiments of the present invention. It is understood that other embodiments may be utilized, and mechanical compositional, structural, electrical, and operational changes may be made without departing from the spirit and scope of the present disclosure. The following detailed description is not to be taken in a limiting sense, and the scope of the embodiments of the present invention is defined only by the claims of the issued patent.

The terminology used herein is for the purpose of describing particular embodiments only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

Figure 1:
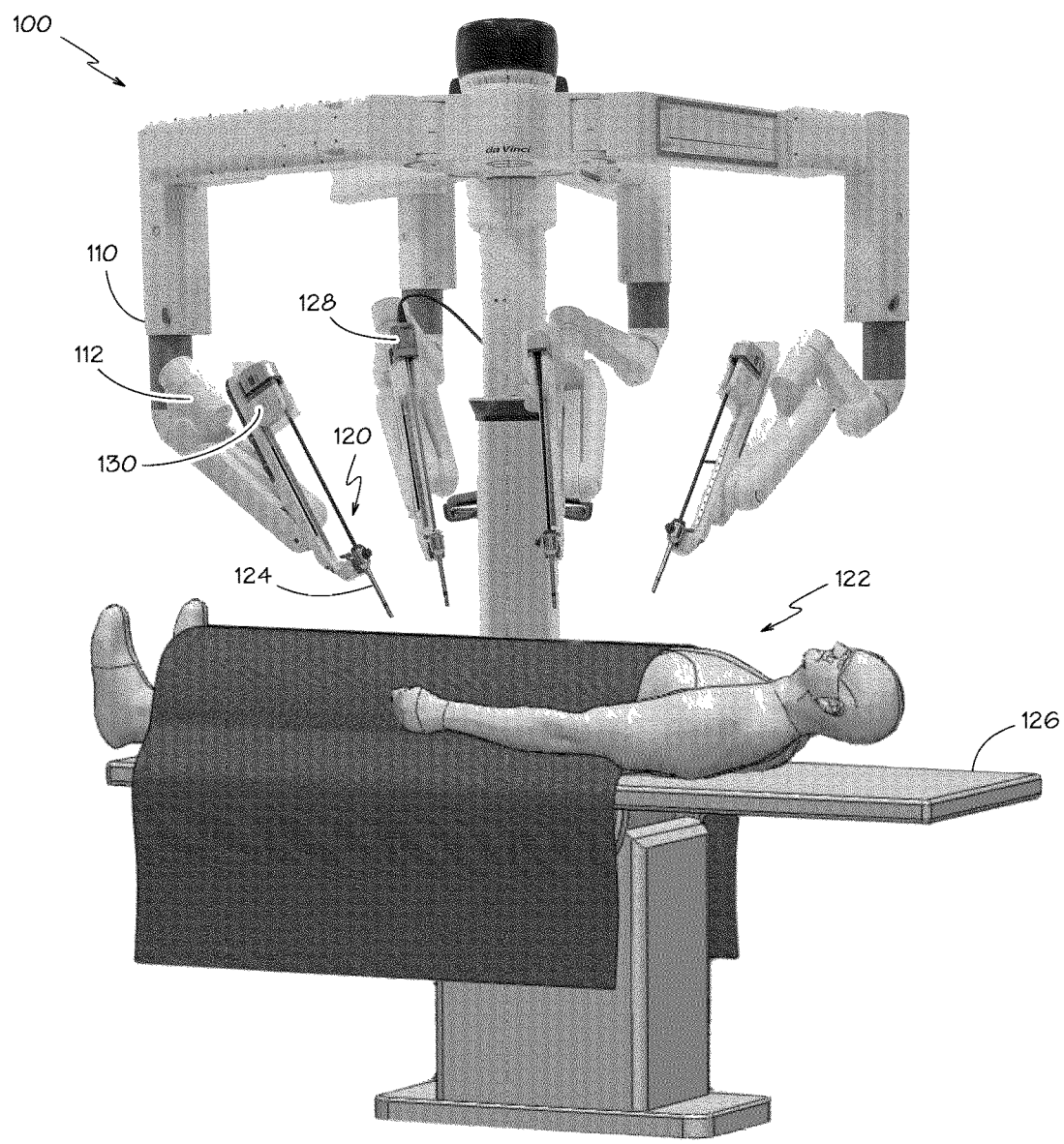
FIG. 1 is a view of an illustrative patient-side portion 100 of a teleoperated surgical system.

FIG. 1 is a view of an illustrative patient-side portion 100 of a teleoperated surgical system, in accordance with embodiments of the present invention. The patient-side portion 100 includes support assemblies 110 and one or more surgical instrument manipulators 112 at the end of each support assembly. The support assemblies optionally include one or more unpowered, lockable setup joints that are used to position the surgical instrument manipulator(s) 112 with reference to the patient for surgery. As depicted, the patient-side portion 100 rests on the floor. In other embodiments the patient-side portion may be mounted to a wall, to the ceiling, to the operating table 126, which also supports the patient's body 122, or to other operating room equipment. Further, while the patient-side portion 100 is shown as including four manipulators 112, more or fewer manipulators 112 may be used. Still further, the patient-side portion 100 may consist of a single assembly as shown, or it may include two or more separate assemblies, each optionally mounted in various possible ways.

Each surgical instrument manipulator 112 supports one or more surgical instruments 120 that operate at a surgical site within the patient's body 122. Each manipulator 112 may be provided in a variety of forms that allow the associated surgical instrument to move with one or more mechanical degrees of freedom (e.g., all six Cartesian degrees of freedom, five or fewer Cartesian degrees of freedom, etc.). Typically, mechanical or control constraints restrict each manipulator 112 to move its associated surgical instrument around a center of motion on the instrument that stays stationary with reference to the patient, and this center of motion is typically located to be at the position where the instrument enters the body.

The term "surgical instrument" is used herein to describe a medical device configured to be inserted into a patient's body and used to carry out surgical or diagnostic procedures. The surgical instrument typically includes an end effector associated with one or more surgical tasks, such as a forceps, a needle driver, a shears, a bipolar cauterizer, a tissue stabilizer or retractor, a clip applier, an anastomosis device, an imaging device (e.g., an endoscope or ultrasound probe), and the like. Some surgical instruments used with embodiments of the invention further provide an articulated support (sometimes referred to as a "wrist") for the end effector so that the position and orientation of the end effector can be manipulated with one or more mechanical degrees of freedom in relation to the instrument's shaft. Further, many surgical end effectors include a functional mechanical degree of freedom, such as jaws that open or close, or a knife that translates along a path. Surgical instruments may also contain stored (e.g., on a semiconductor memory inside the instrument) information that may be permanent or may be updatable by the surgical system. Accordingly, the system may provide for either one-way or two-way information communication between the instrument and one or more system components.

A functional teleoperated surgical system will generally include a vision system portion (not shown) that enables the operator to view the surgical site from outside the patient's body 122. The vision system typically includes a surgical instrument that has a video-image-capture function 128 (a "camera instrument") and one or more video displays for displaying the captured images. In some surgical system configurations, the camera instrument 128 includes optics that transfer the images from the distal end of the camera instrument 128 to one or more imaging sensors (e.g., CCD or CMOS sensors) outside of the patient's body 122. Alternatively, the imaging sensor(s) may be positioned at the distal end of the camera instrument 128, and the signals produced by the sensor(s) may be transmitted along a lead or wirelessly for processing and display on the video display. An illustrative video display is the stereoscopic display on the surgeon's console in surgical systems commercialized by Intuitive Surgical, Inc., Sunnyvale, Calif.

A functional teleoperated surgical system will further include a control system portion (not shown) for controlling the movement of the surgical instruments 120 while the instruments are inside the patient. The control system portion may be at a single location in the surgical system, or it may be distributed at two or more locations in the system (e.g., control system portion components may be in the system's patient-side portion 100, in a dedicated system control console, or in a separate equipment rack). The teleoperated master/slave control may be done in a variety of ways, depending on the degree of control desired, the size of the surgical assembly being controlled, and other factors. In some embodiments, the control system portion includes one or more manually-operated input devices, such as a joystick, exoskeletal glove, a powered and gravity-compensated manipulator, or the like. These input devices control teleoperated motors which, in turn, control the movement of the surgical instrument.

The forces generated by the teleoperated motors are transferred via drivetrain mechanisms, which transmit the forces from the teleoperated motors to the surgical instrument 120. In some telesurgical embodiments, the input devices that control the manipulator(s) may be provided at a location remote from the patient, either inside or outside the room in which the patient is placed. The input signals from the input devices are then transmitted to the control system portion. Persons familiar with telemanipulative, teleoperative, and telepresence surgery will know of such systems and their components, such as the da Vinci® Surgical System commercialized by Intuitive Surgical, Inc. and the Zeus® Surgical System originally manufactured by Computer Motion, Inc., and various illustrative components of such systems.

As shown, both the surgical instrument 120 and an optional entry guide 124 (e.g., a cannula in the patient's abdomen) are removably coupled to the distal end of a manipulator 112, with the surgical instrument 120 inserted through the entry guide 124. Teleoperated actuators in the manipulator 112 move the surgical instrument 112 as a whole. The manipulator 112 further includes an instrument carriage 130. The surgical instrument 120 is detachably connected to the carriage 130. The teleoperated actuators housed in the carriage 130 provide a number of controller motions which the surgical instrument 120 translates into a variety of movements of the end effector on the surgical instrument. Thus the teleoperated actuators in the carriage 130 move only one or more components of the surgical instrument 120 rather than the instrument as a whole. Inputs to control either the instrument as a whole or the instrument's components are such that the input provided by a surgeon to the control system portion (a "master" command) is translated into a corresponding action by the surgical instrument (a "slave" response).

Figure 2:
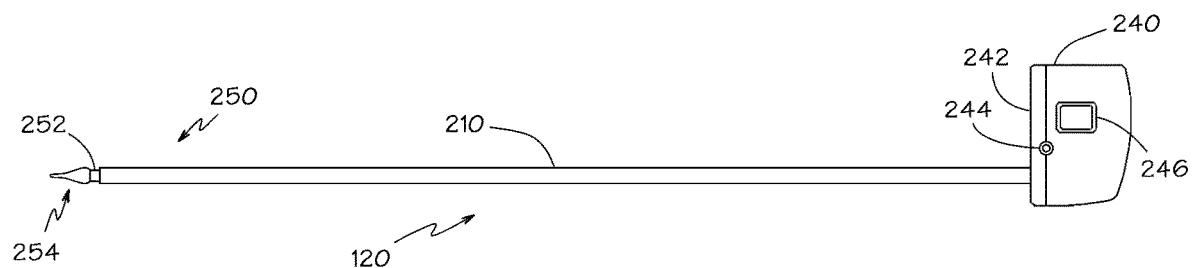
FIG. 2 is a side view of a surgical instrument for use with a teleoperated actuator.

FIG. 2 is a side view of an illustrative embodiment of the surgical instrument 120, comprising a distal portion 250 and a proximal control mechanism 240 coupled by an elongate tube 210. The distal portion 250 of the surgical instrument 120 may provide any of a variety of end effectors such as the forceps 254 shown, a needle driver, a cautery device, a cutting tool, an imaging device (e.g., an endoscope or ultrasound probe), or a combined device that includes a combination of two or more various tools and imaging devices. In the embodiment shown, the end effector 254 is coupled to the elongate tube 210 by a "wrist" 252 that allows the orientation of the end effector to be manipulated with reference to the instrument tube 210.

Referring again to FIG. 1, a surgical instrument 120, its related actuators 130, and support structure may be supported vertically by an extensible support 110.

FIG. 3 is a side view of the extensible support 110. A vertical column 300 hangs down from a housing. An arm 304 is supported by the lower end 306 of the vertical column 300. The arm in turn supports the surgical manipulator and its associated teleoperated actuators. A surgical instrument may be coupled to the surgical manipulator and be supported in turn by the arm 304 and the vertical column 300.

FIG. 4 is a side view of the extensible support 110 shown in FIG. 3 with the cover 302 removed from the housing. The upper end 410 of the vertical column 300 is coupled to a sliding assembly, such as a track 408 and carriage 406 assembly that allows the vertical column to move up and down to adjust the height of the surgical manipulator over the patient.

FIG. 5 is a perspective view of the housing portion of the extensible support shown in FIG. 4. Some components have been removed to allow the track 408 and carriage 406 assembly to be seen more clearly.

Referring again to FIG. 4, a constant force spring 400 is coupled to the vertical column 300 at a lower end 402 of the constant force spring. The constant force spring 400 is rolled around a drum 404 that is supported by the upper end of the extensible support assembly 110. The constant force spring counteracts the force of gravity acting on the vertical column 300 and the structures it supports including the surgical instrument.

Constant force springs may be constructed as a rolled ribbon of spring steel such that the spring is relaxed at a lower stress state when rolled up as opposed to being extended. As it is unrolled, the restoring force comes primarily from the portion of the ribbon near the roll of relaxed spring. Specifically, the force comes from the region that is being transitioned from round to flat. No force comes from the portion that is totally unrolled, or still rolled on the drum. Because the geometry of that region remains nearly constant as the spring unrolls, the resulting force is nearly constant. A self-retracting steel measuring tape is an example of a constant force spring. While the constant force spring 400 provides a nearly constant counterbalancing force to support vertical column 300 and the attached structures, it would desirable to provide a counterbalancing force that is more constant than what can be achieved with a constant force spring alone and which can compensate for differing supported weights.

Figure 6:
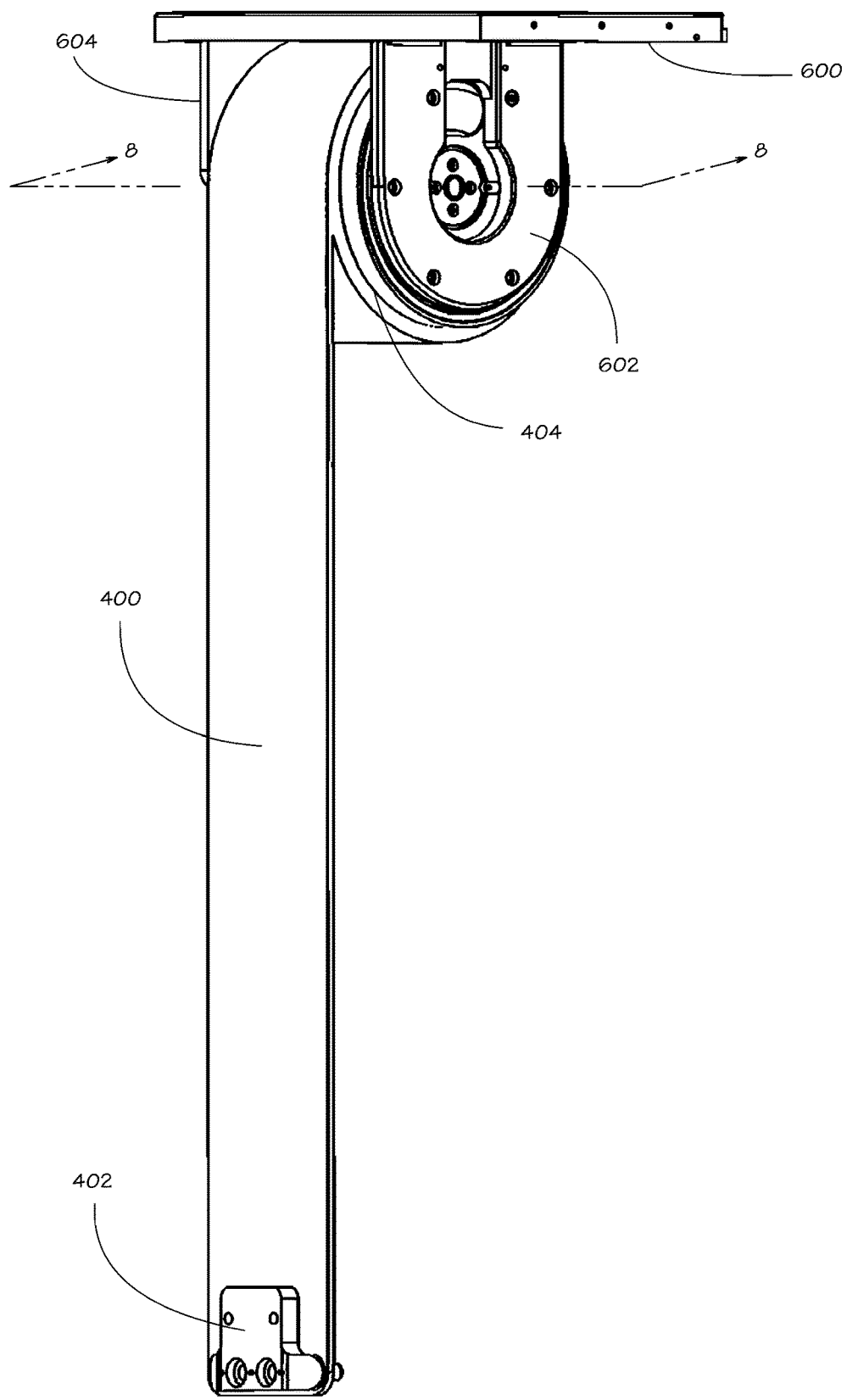
FIG. 6 is a perspective view of a constant force spring assembly.

FIG. 6 is a perspective view of the constant force spring 400 shown in FIG. 4. A bracket 600, 602, 604 is supported by the upper end of the extensible support assembly 110. The bracket rotatably supports the drum 404 around which the constant force spring 400 is rolled. The constant force spring 400 may be fixed to the drum by the friction force created between the surface of the drum and the constant force spring as it attempts to fully roll up to a relaxed diameter that is smaller than the drum diameter.

Figure 7:
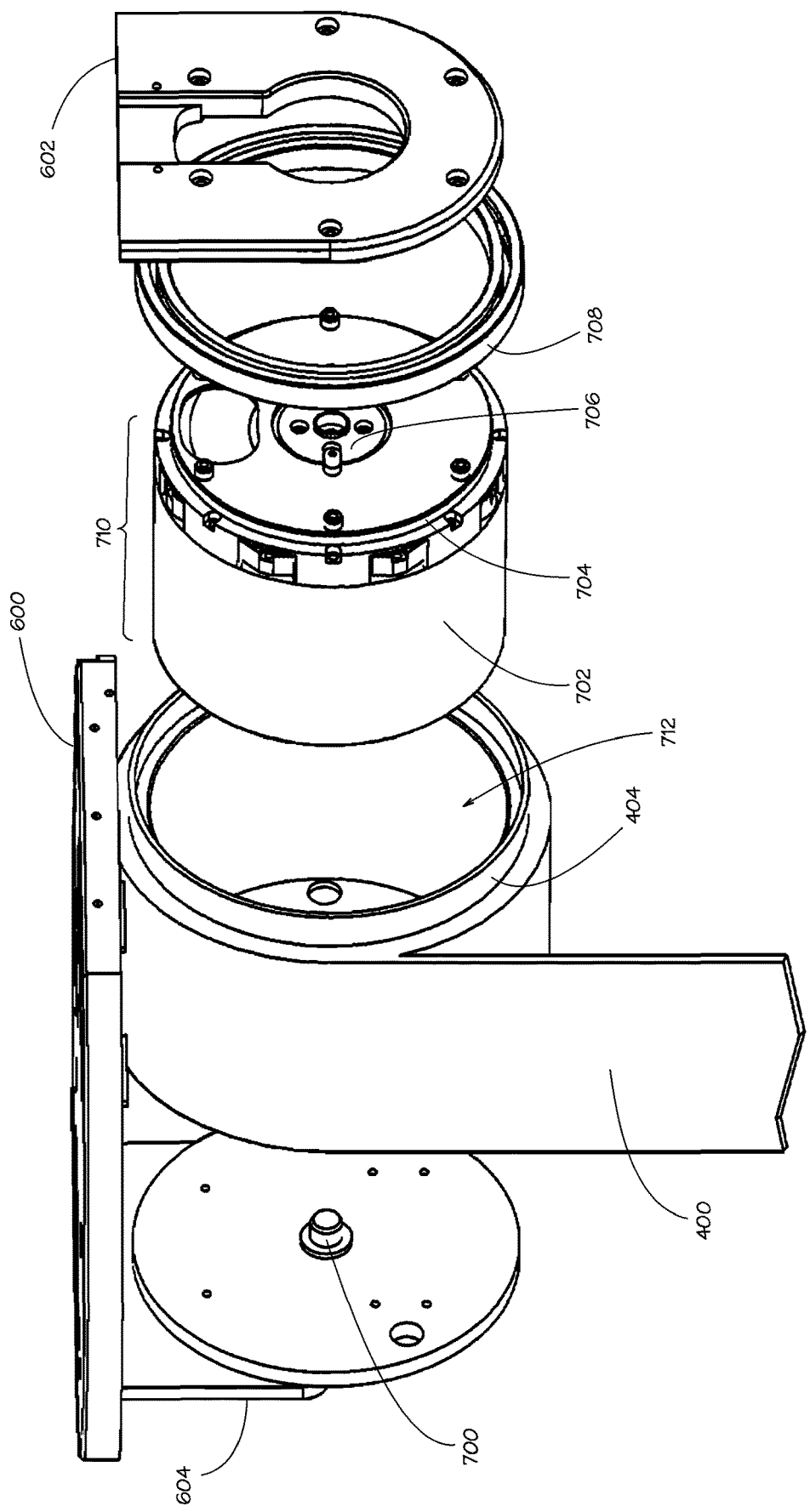
FIG. 7 is an exploded perspective view of a portion of the constant force spring assembly shown in FIG. 6.

FIG. 7 is an exploded view of the drum portion of the constant force spring assembly shown in FIG. 5. A plate that includes an axial support 700 is fixed to one side 604 of the bracket that supports the drum 404 from the upper end of the extensible support assembly 110. The axial support 700 may provide a bearing that rotatably supports the drum 404. The constant force spring assembly includes a motor 710, which may be a brushless DC motor, having a stator 702 and a rotor 706 that provides an active rotational force that turns the drum 404. The force provided by the motor is translated into a linear force acting on the vertical column 300. The torque provided by the motor is translated into a linear force across the constant force spring acting on the vertical column 300. The torque provided by the motor may add to or subtract from the counterbalancing force provided by the constant force spring 400.

The motor includes a stator 702 that is fixed to a second side 602 of the bracket that supports the drum 404. A bearing 708 may be supported by a portion 704 of the motor stator to provide a rotatable support for the drum 404. The motor further includes a rotor 706 that is fixed to the drum 404.

Figure 8:
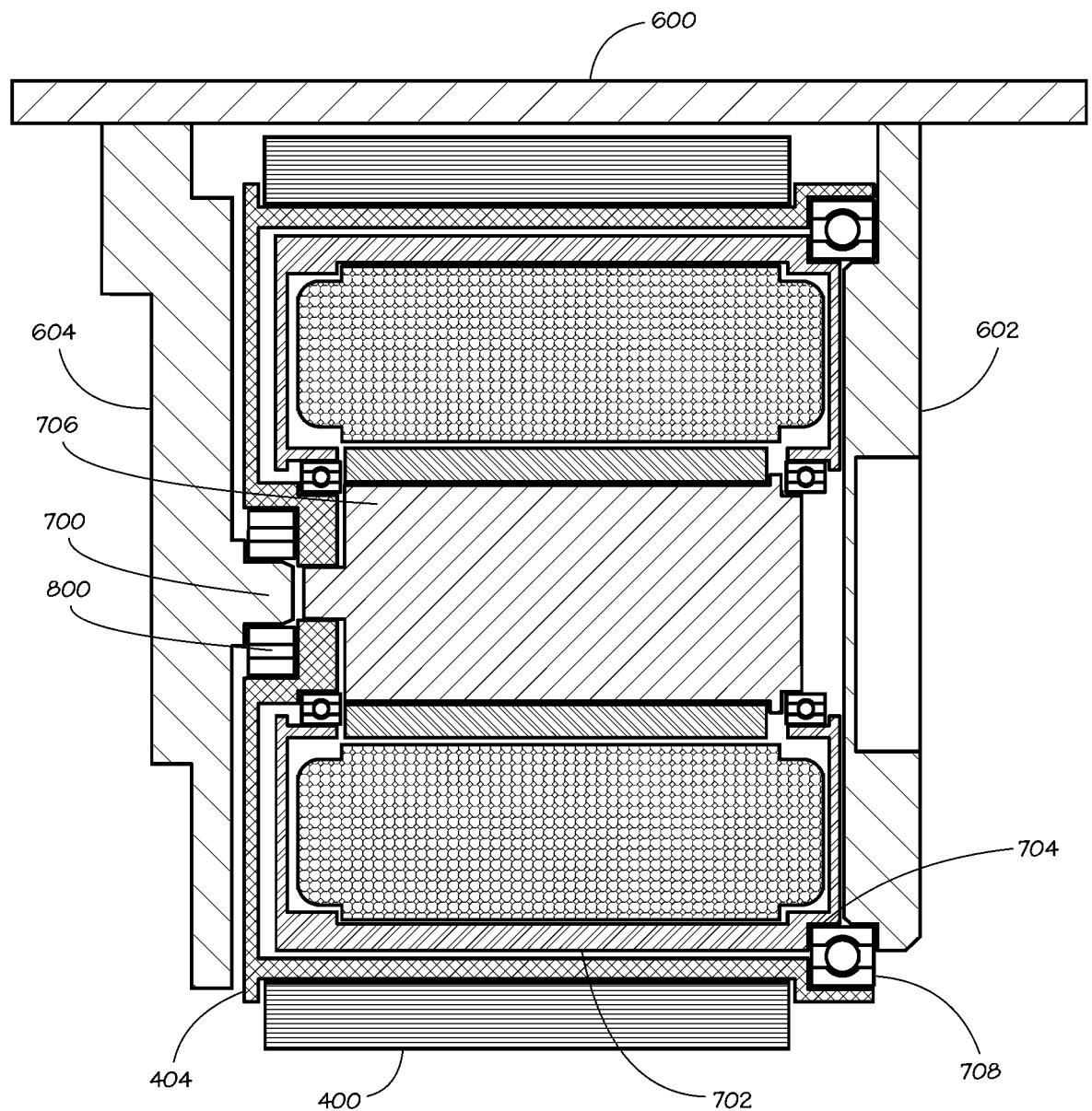
FIG. 8 is a cross-section view of a portion of the constant force spring assembly taken along line 8-8 in FIG. 6.

FIG. 8 is cross-section view of the drum portion of the constant force spring assembly taken along section line 8-8 shown in FIG. 6. As can be seen in this view, the bracket 600, 602, 604 and the motor stator 702 are fixed together as one sub-assembly. The bracket and motor stator 702 provide a ground reference for the rotating drum 404 and motor rotor 706 which are fixed together as a second sub-assembly.

A first bearing 800 that is supported by the axial support 700 on the bracket 604 supports a closed end of the drum 404. Providing a closed end to the drum 404 may increase the strength of the drum so that it can support the rolling force of the constant force spring 400 when rolled onto the drum prior to being assembled with the motor. A second bearing 708 that is supported by a shoulder 704 on the motor stator 702 supports an open end of the drum 404. Thus the drum 404 and motor rotor 706 are supported by bearings 708, 800 that are in turn supported by the grounded bracket 600,602, 604 and motor stator 702. Thus the motor 710 is located in an interior volume 712 of the drum 404. In other embodiments, other arrangements may be used to rotatably support the drum and motor rotor with respect to the bracket and motor stator.

Figure 9:
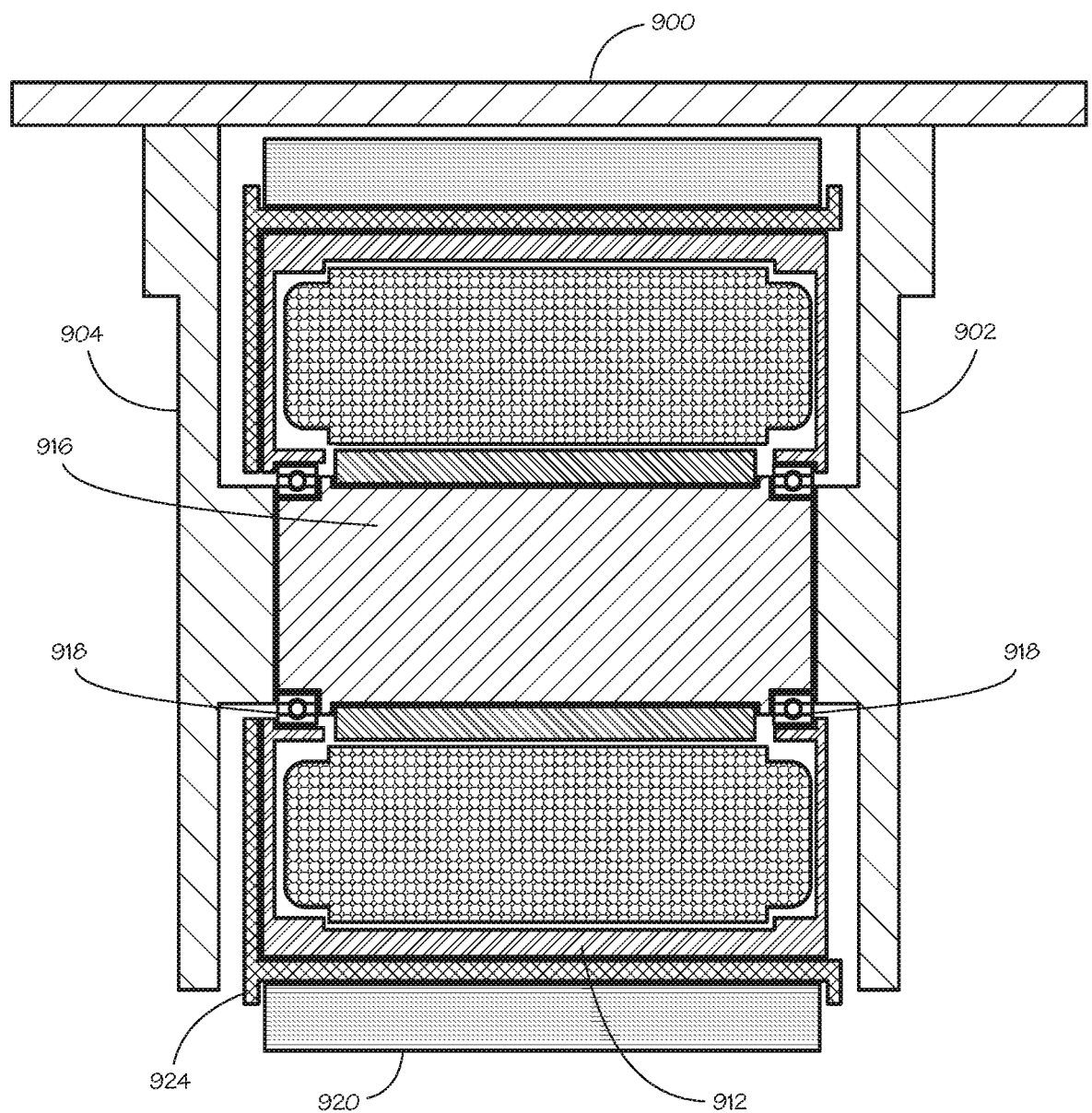
FIG. 9 is a cross-section view of a portion of another embodiment of the constant force spring assembly.

FIG. 9 is cross-section view of a drum portion of another constant force spring assembly taken along a section line corresponding to section line 8-8 shown in FIG. 6. In this embodiment, what has been identified as the motor rotor 916 is fixed to the bracket 900, 902, 904 and the drum 924 is coupled to what has been identified as the motor stator 912. As can be seen in this view, the bracket 900, 902, 904 and the motor rotor 916 are fixed together as one sub-assembly. The bracket and motor provide a ground reference for the rotating drum 904 and motor stator 902 which are fixed together as a second sub-assembly. In this configuration the outer part of the motor and the coupled drum rotate around the inner part of the motor.

In other embodiments, the motor may be provided in locations other than the interior volume of the drum that supports the constant force spring. For example, the rotor of the motor may be extended by a shaft that is directly coupled to the coaxial drum. Alternatively, the drum and the motor may not be coaxial and the rotor of the motor may be coupled to the drum by a mechanical transmission such as a belt, gears, and/or a chain and sprocket drive.

It will be appreciated that the constant force spring could be replaced by a flat belt and the motor could provide the force to counterbalance the force of gravity acting on the vertical column 300 and the structures it supports including the surgical instrument. However, this would require a sizeable motor and a substantial amount of electric current to support mechanisms that may weigh perhaps twelve to twenty-four kilograms. By providing a constant force spring as the coupling between the motorized drum and the load, the constant force spring provides the majority of the force required to support the load. The motor provides a biasing force that corrects for the variability of the load and the irregularities in the force provided by the constant force spring.

In one embodiment, the constant force spring is sized to provide slightly more than the force required to support the heaviest load. Thus the constant force spring will always lift the load. The motor is used to provide a controllable downward force that acts against the force provided by the constant force spring to provide a "neutral buoyancy" for the vertical column and the structures it supports.

Figure 10:
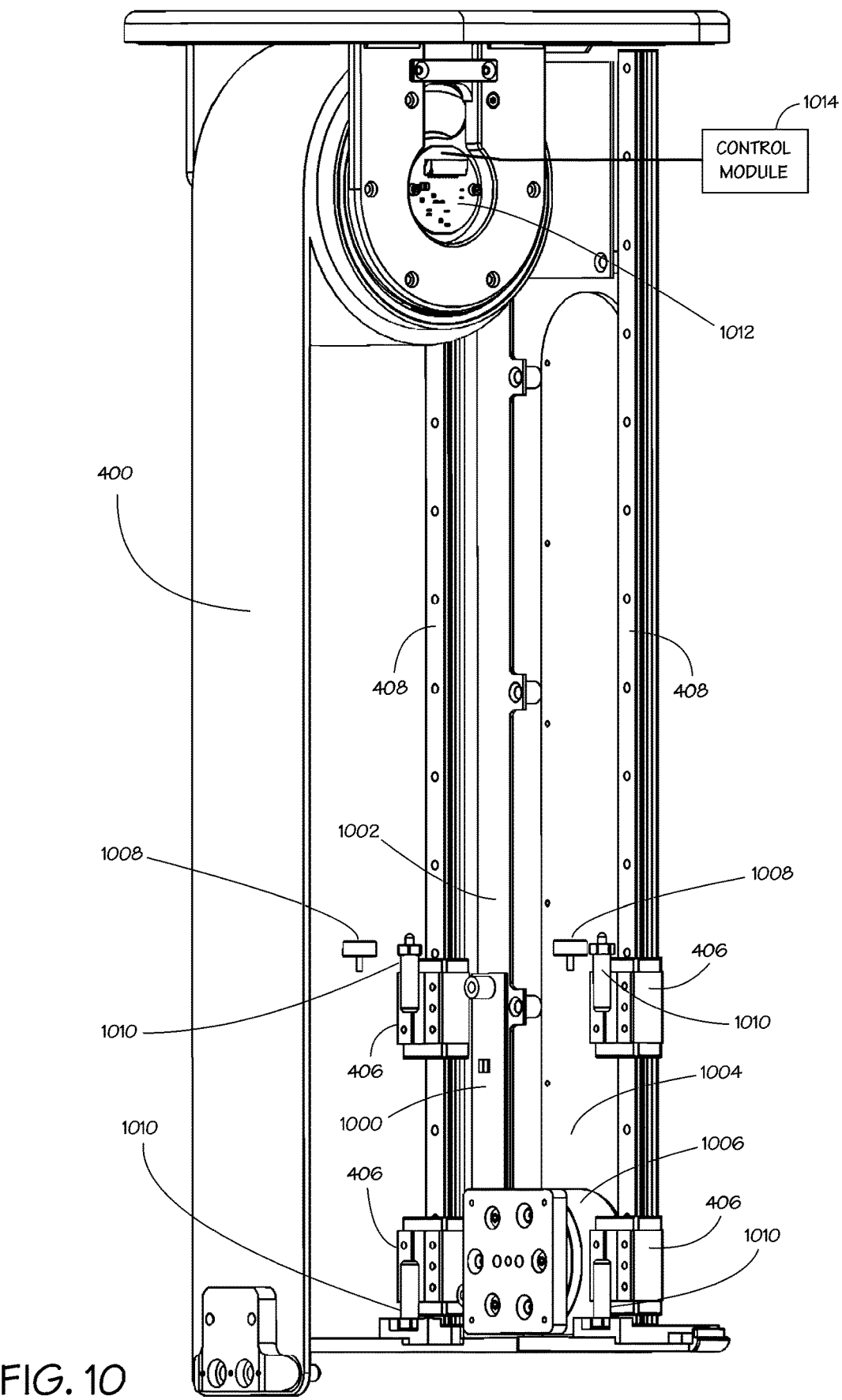
FIG. 10 is a perspective view of a constant force spring assembly with additional components of the setup joint.

FIG. 10 is a perspective view of the constant force spring 400 shown in FIG. 6 with additional components shown. As previously discussed, the vertical column may be supported by a track 408 and carriage 406 assembly. A brake may be provided to hold the vertical column in a fixed position so that no power is required when the position of the vertical column is not being changed. The brake may be in the form of a brake that clamps the extended portion of the constant force spring in a fixed position, a brake that prevents the drum from rotating, or a brake that prevents the vertical column from moving, such as the magnetic brake illustrated that magnetically grips an armature 1004 with a magnetic brake shoe 1006.

The motor includes a primary sensor 1012, which is a rotary sensor that provides an absolute rotary position for the motor. One part of the primary sensor is mounted on the motor rotor. The other part of the primary sensor is mounted to a mechanical ground, such as the motor stator. The primary sensor is coupled to a control module 1014 that provides controlled electrical current to the motor to provide the desired motion and torque from the motor. The primary sensor is used for motor commutation and shaft speed control.

A secondary sensor 1000, 1002 may be provided to provide data for the position of the vertical column to the control module 1014. The secondary sensor 1000, 1002 may be mounted to the carriage that supports the vertical column and to a mechanical ground such as the frame that supports the stationary rails 408 on which the carriage slides. The secondary sensor 1000, 1002 provides an absolute linear position.

The secondary sensor 1000, 1002 provides a backup to the primary sensor 1012. Readings from the two sensors may be compared to confirm that the vertical column as sensed by the secondary sensor 1000, 1002 is moving as expected based on the rotation of the motor as sensed by the primary sensor 1012.

The secondary absolute position sensor 1000, 1002 may be used to periodically calibrate the force required to compensate for irregularities in the force provided by the constant force spring 400 and for fatigue of the spring resulting from extended use. The calibration routine uses the secondary sensor 1000, 1002 in conjunction with the motor and the primary motor sensor 1012. Because the effective radius of the constant force spring 400 is a function of how much is payed out, the ratio between the primary and secondary sensors is variable. This variable ratio is taken into consideration in the calibration. Such calibration will generally be needed infrequently.

Instruments supported by the vertical column may be provided with machine readable identification that enables the control module 1014 to determine the amount of weight added to the vertical column by the instrument. The machine readable identification may provide a general weight for the type of instrument or a specific weight for the individual instrument, either directly or by reference to a database of instrument information. The control module 1014 is able to adjust the electrical current provided to the motor to provide the desired force from the motor to compensate for the weight of the installed surgical instrument.

The track 408 and carriage 406 assembly includes mechanical stops to prevent the carriages from running off the tracks. The mechanical stops may include rubber bumpers 1008 that limit the carriage motion with only a small amount of material deformation, perhaps 1 to 1.5 mm. The mechanical stops may also include spring stops 1010 that limit the carriage motion while providing a greater amount of yield, perhaps 3 to 3.5 mm. It will be appreciated that even the spring stops 1010 may stop the carriage somewhat abruptly.

It may be desirable to provide some low compliance movement at the ends of the range of motion of the carriage 406 during operating table 126 motion. If the carriage 406 is at the end of its range of motion, operating table 406 motion may not be possible. If the carriage 406 reaches a mechanical stop 1008, 1010 during operating table 126 motion, the ability to move the operating table further is eliminated. The spring plunger 1010 may be allowed to push the carriage 406 off the limit of the mechanical stops 1008, 1010 to bring the carriage to rest at a position that allows for low compliance movement of the carriage in both directions. It may be desirable to provide for mechanical brakes that hold the carriage in a fixed position. The brakes may be applied through software control that prevents brake application when the spring plungers 1010 are depressed. Therefore the software system lets the spring plungers 1010 push the carriage 406 off the mechanical stops 1008, 1010 before applying the brakes.

The control module 1014 may use the motor to resist movement toward the end of the range of travel and bring the carriage to a stop over a greater distance to avoid abruptly stopping the movement of the carriage. The control software implemented stop may gradually increase the force required to move the carriage assembly over the end of the range of carriage travel, perhaps over the final 12 to 20 mm of carriage travel. The increase in force provided by the motor to resist motion through the end of the range of travel for the carriage may be applied non-linearly to stop the carriage with a desired deceleration profile. The software implemented stop may provide a force that gradually increases from a zero force at the beginning of the range, something that may be difficult to implement with a mechanical stop.

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. The description is thus to be regarded as illustrative instead of limiting.

What is claimed is:

1. A compensated constant force spring device comprising:
   a bracket;
   a drum rotatably coupled to the bracket;
   a constant force spring coupled to the drum; and
   a motor having a rotor coupled to the bracket and a stator coupled to the drum.

2. The compensated constant force spring device of claim 1 further comprising a control module coupled to the motor.

3. The compensated constant force spring device of claim 2 further comprising a position sensor coupled to the control module, wherein the control module causes the motor to provide a force responsive to a signal from the position sensor.

4. The compensated constant force spring device of claim 3 further comprising a secondary position sensor coupled to the control module, wherein the control module compares the signal from the position sensor to a secondary signal from the secondary position sensor to calibrate the force to be provided by the motor.

5. The compensated constant force spring device of claim 1 wherein the motor is located in an interior volume of the drum.

6. An extensible support device comprising:
   a bracket;
   a sliding assembly fixed to the bracket;
   a vertical column coupled to the sliding assembly at an upper end and supporting a load at a lower end, the sliding assembly allowing the vertical column to move in a vertical direction;
   a drum rotatably coupled to the bracket;
   a constant force spring having a first end coupled to the drum and a second end coupled to the vertical column, the constant force spring counterbalancing gravitational forces on the vertical column; and
   a motor having a rotor coupled to the bracket and a stator coupled to the drum.

7. The extensible support device of claim 6 further comprising a control module coupled to the motor.

8. The extensible support device of claim 7 further comprising a position sensor coupled to the control module, wherein the control module causes the motor to provide a force responsive to a signal from the position sensor.

9. The extensible support device of claim 8 further comprising a secondary position sensor coupled to the control module, wherein the control module compares the signal from the position sensor to a secondary signal from the secondary position sensor to calibrate the force to be provided by the motor.

10. The extensible support device of claim 8 wherein the control module further causes the motor to provide an additional force when the signal from the position sensor indicates that the vertical column is approaching an end of a range of travel.

11. The extensible support device of claim 6 wherein the motor is located in an interior volume of the drum.

12. An extensible support device comprising:
    a bracket;
    a motor coupled to the bracket;
    a drum coupled to the motor such that the drum can rotate with respect to the bracket;
    means for supporting a load that is movable in a vertical direction;
    a constant force spring coupled to the drum at a first end and coupled to the means for supporting the load at a second end, the constant force spring counterbalancing gravitational forces on the load; and
    a control module coupled to the motor to apply a controlled compensating force to the drum.

13. The extensible support device of claim 12 further comprising:
    first means for sensing a position of the load; and
    means for adjusting the controlled compensating force responsive to the position of the load.

14. The extensible support device of claim 13 further comprising:
    second means for sensing the position of the load; and
    means for to calibrating the controlled compensating force by comparing signals from the first and second means for sensing the position of the load.

15. The extensible support device of claim 13 further comprising means for further adjusting the controlled compensating force when the load is approaching an end of a range of travel.

16. A method for supporting a load that is movable in a vertical direction, the method comprising:
    supporting the load from a lower end of a vertical column;
    supporting an upper end of the vertical column on a sliding assembly fixed to a bracket;
    coupling a motor to the bracket;
    coupling a drum to the motor such that the drum can rotate with respect to the bracket;
    coupling a first end of a constant force spring to the drum;
    coupling a second end of the constant force spring to the vertical column to counterbalance gravitational forces on the vertical column; and
    applying a controlled compensating force to the drum with the motor.

17. The method of claim 16 wherein the motor has a rotor coupled to the bracket and a stator coupled to the drum.

18. The method of claim 16 wherein the motor has a stator coupled to the bracket and a rotor coupled to the drum.

19. The method of claim 16 further comprising:
    sensing a position of the load with a position sensor; and adjusting the controlled compensating force responsive to the position of the load.

20. The method of claim 19 further comprising:
sensing the position of the load with a secondary position sensor; and
comparing the position of the load from the position sensor to the position of the load from the secondary position sensor to calibrate the controlled compensating force to be provided.

21. The method of claim 19 further comprising adjusting the controlled compensating force when the load is approaching an end of a range of travel.

* * * * *